US010045515B2

(12) United States Patent
Cooper

(10) Patent No.: US 10,045,515 B2
(45) Date of Patent: Aug. 14, 2018

(54) EDIBLE, RETRIEVABLE ANIMAL ITEMS

(71) Applicant: Jeffrey T Cooper, Orlando, FL (US)

(72) Inventor: Jeffrey T Cooper, Orlando, FL (US)

( * ) Notice: Subject to any disclaimer, the term of this patent is extended or adjusted under 35 U.S.C. 154(b) by 0 days.

(21) Appl. No.: 15/452,466

(22) Filed: Mar. 7, 2017

(65) Prior Publication Data

US 2017/0251637 A1 Sep. 7, 2017

Related U.S. Application Data

(60) Provisional application No. 62/304,914, filed on Mar. 7, 2016.

(51) Int. Cl.
| | | |
|---|---|---|
| *A01K 15/02* | (2006.01) | |
| *A23K 50/42* | (2016.01) | |
| *A61K 31/352* | (2006.01) | |
| *A61Q 11/00* | (2006.01) | |
| *A61K 8/97* | (2017.01) | |
| *A61K 8/02* | (2006.01) | |
| *A61K 35/60* | (2006.01) | |
| *A61K 31/202* | (2006.01) | |
| *A61K 36/185* | (2006.01) | |
| *A61K 31/05* | (2006.01) | |
| *A23K 40/30* | (2016.01) | |

(52) U.S. Cl.
CPC ............ *A01K 15/026* (2013.01); *A23K 40/30* (2016.05); *A23K 50/42* (2016.05); *A61K 8/0233* (2013.01); *A61K 8/97* (2013.01); *A61K 31/05* (2013.01); *A61K 31/202* (2013.01); *A61K 31/352* (2013.01); *A61K 35/60* (2013.01); *A61K 36/185* (2013.01); *A61Q 11/00* (2013.01)

(58) Field of Classification Search
None
See application file for complete search history.

(56) References Cited

U.S. PATENT DOCUMENTS

| | | | | |
|---|---|---|---|---|
| 5,004,624 | A * | 4/1991 | Koschak | A23K 40/20 426/623 |
| 5,200,218 | A | 4/1993 | Lasater et al. | |
| 6,379,725 | B1 * | 4/2002 | Wang | A01K 15/026 426/104 |
| 6,546,896 | B1 * | 4/2003 | Markham | A01K 15/026 119/709 |
| 6,672,252 | B2 * | 1/2004 | Levin | A01K 15/026 119/709 |
| 7,485,330 | B2 * | 2/2009 | Anderson | A23K 50/40 426/656 |
| 8,496,981 | B2 | 7/2013 | Zicker et al. | |
| 9,398,757 | B2 | 7/2016 | Reynolds | |
| 2003/0012861 | A1 * | 1/2003 | Mayer | A23C 11/103 426/629 |
| 2004/0049059 | A1 * | 3/2004 | Mueller | A61K 31/35 549/390 |
| 2006/0121162 | A1 * | 6/2006 | Garrett | A23K 40/20 426/132 |
| 2012/0058227 | A1 | 3/2012 | Keehn et al. | |
| 2013/0104810 | A1 | 5/2013 | Haakansson et al. | |
| 2015/0013616 | A1 | 1/2015 | Tsengas | |

OTHER PUBLICATIONS

Petstages, available online at: http://www.drsfostersmith.com/product/prod_display.cfm?pcatid=25214, downloaded on Sep. 8, 2017, published online on Nov. 16, 2012, pp. 1-2.*

* cited by examiner

*Primary Examiner* — Abigail Vanhorn
(74) *Attorney, Agent, or Firm* — Monty Simmons; Simmons Patents

(57) ABSTRACT

A flavored or unflavored pet treat-item using hemp based products and byproducts constructed to be eaten by a pet as a treat in one to two days. The outer shell of the treat-item is patterned after natural tree bark such as Pine, Cypress, Redwood and Oak. The treat-item contains supplements that provide pets the beneficial support from cannabanoids such as CBAs, CBDs and CBNs for which may help treatment of ailments such as arthritis, hip pain, tumors, leukemia, cancers, organ tissue repair and neurological regeneration; as well as, fiber support for teeth and digestive system health. A viscous version of the product in the form of baby food may be produced for tube feeding pets with more advanced debilitations.

19 Claims, 8 Drawing Sheets

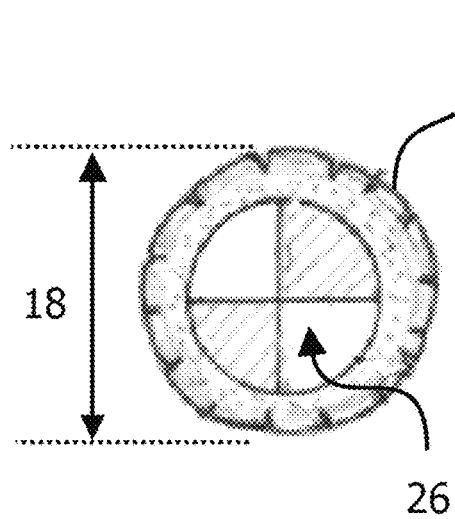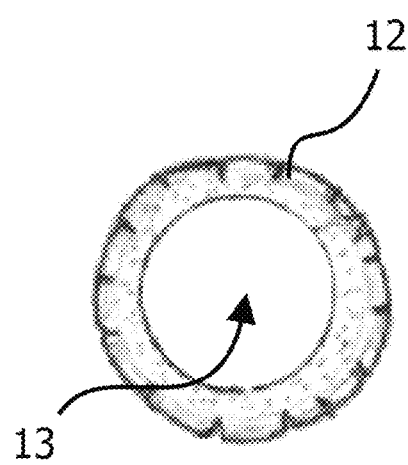
Fig. 3   Fig. 4
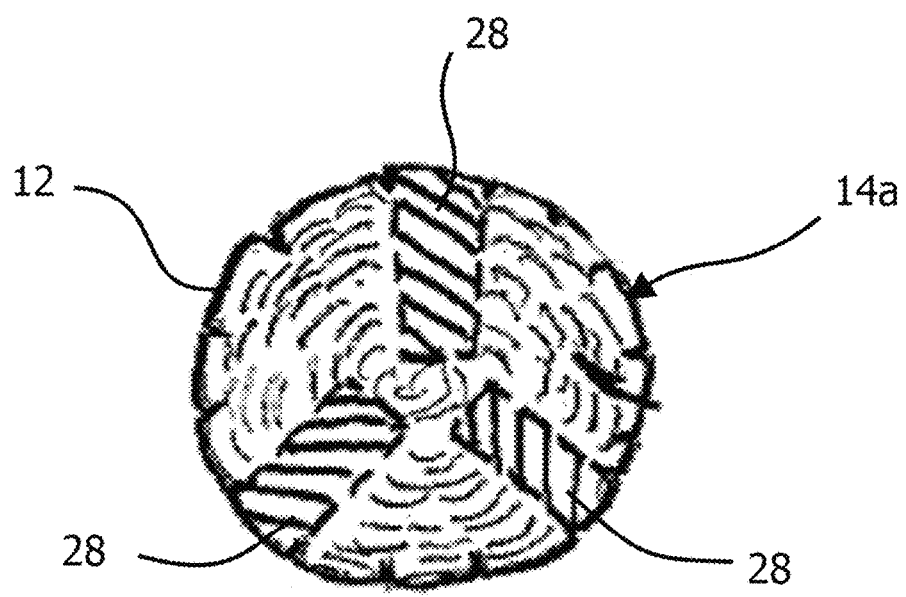
Fig. 5

Cypress bark

Oak Bark

Redwood Bark

Pine Bark

EDIBLE, RETRIEVABLE ANIMAL ITEMS

CLAIM TO PRIORITY

This application claims priority to provisional application 62/304,914, filed on 7 Mar. 2016 of which the entire contents of such document is incorporated herein by this reference for all that the document discloses for all purposes.

TECHNICAL FIELD

The invention relates to the primary field of edible items (such as treats) for animals wherein such items can be used as a pet toy, until consumed, thereby creating a retrievable, edible animal item. Disclosed are flavored and unflavored retrievable, edible pet treats (e.g. dogs and cats) formed from a high fibrous vegetable or plant material and byproducts formed in the shape of sticks, with/without bark patterns, branches and/or wood textures.

BACKGROUND OF THE INVENTION

It was not until the mid-1800s that the world saw its first food made specifically for dogs when James Spratt concocted the first dog treat. Living in London at the time, he witnessed dogs around a shipyard eating scraps of discarded biscuits. Shortly thereafter he introduced his dog food, made up of wheat meals, vegetables and meat. By 1890 production had begun in the United States and became known as "Spratt's Patent Limited". In later years, the dog biscuit was sometimes treated as synonymous with dog food. Today, dog treats are considered special types of dog food given as a reward, not as a staple food source.

A large percentage of homes have at least one pet, typically a dog or cat and such pets are often considered a "member of the family". Consequently, dog owners, for example, often give their dog treats and purchase all kinds of pet toys for their dogs/pets to play with. Prior art products, however, do not effectively combine the two items.

Additionally, while officials at the U.S. Food and Drug Administration and Association of American Feed Control set standards for pet food ingredient safety, many dog foods and treats are not healthy for dogs. For example, a large percentage of prior art dog biscuits contain wheat as the first/major ingredient. We know that wheat contains high amounts of gluten and the digestive systems of dogs have not evolved to digest plant proteins such as gluten. Feeding dogs foods that contain too much gluten can result in many of the same problems that afflict humans who are sensitive to gluten.

Embodiments of the disclosed invention address at least the above described nutritional issues while combining a pet treat with a toy function.

SUMMARY OF THE INVENTION

Some of the objects and advantages of the invention will now be set forth in the following description, while other objects and advantages of the invention may be obvious from the description or may be learned through practice of the invention.

Broadly speaking, a principle object of the present invention is to provide a combination retrievable treat-item constructed from a durable vegetative and fibrous material utilizing an autoclave curing process to give the invention a structural composition that allows an animal to interact with (attack, play) the treat-item without the treat-item "immediately" breaking apart. Thus, unlike prior art treats and toys, embodiments of the current invention will not only define a toy-item but will ideally allow a pet to ultimately consume (hours, days, not minutes) the toy-item like a typical pet treat or bone.

Another general object of the invention is to provide for flavored or unflavored edible items for dogs and cats using hemp-based products and byproducts preferably formed in the shape of a toy. The "HempBone" is composed at least partially of hemp to provide pets the beneficial support from cannabinoids such as Cannabidiol (CBDs) and cannabinol (CBNs) for treatment of pet ailments such as arthritis, hip pain, tumor shrinking, leukemia, cancers and organ tissue regeneration; as well as, fiber support for teeth and digestive system health. A viscous version of the product in the form of baby food may be produced for tube feeding pets with more advanced debilitations. Wherever and whenever possible and practical, natural organic processes will be utilized to produce the highest quality results.

Additional embodiments of the invention are configured to allow for delivery of supplements and/or treatments within a center cavity of a "pet toy". Such supplements address issues including joint health support, flea and tick treatment, heart worm treatment, bone density, digestive health, eye support supplements or any other nutrition aids which are beneficial to general health and/or well-being of the animal of interest. For one embodiment, the texturing of the surface of treat-item resembles the bark of various tree species and are configured in a way to over accentuate the recesses and peaks to provide a teeth cleaning benefit for the pet although such bark features are directed mainly by appearance.

Additional objects and advantages of the present invention are set forth in the detailed description herein or will be apparent to those skilled in the art upon reviewing the detailed description. Also, it should be further appreciated that modifications and variations to the specifically illustrated, referenced, and discussed steps, or features hereof may be practiced in various uses and embodiments of this invention without departing from the spirit and scope thereof, by virtue of the present reference thereto. Such variations may include, but are not limited to, substitution of equivalent steps, referenced or discussed, and the functional, operational, or positional reversal of various features, steps, parts, or the like. Still further, it is to be understood that different embodiments, as well as different presently preferred embodiments, of this invention may include various combinations or configurations of presently disclosed features or elements, or their equivalents (including combinations of features or parts or configurations thereof not expressly shown in the figures or stated in the detailed description).

Those of ordinary skill in the art will better appreciate the features and aspects of such embodiments, and others, upon review of the remainder of the specification.

BRIEF DESCRIPTION OF THE DRAWINGS

A full and enabling description of the present subject matter, including the best mode thereof, directed to one of ordinary skill in the art, is set forth in the specification, which makes reference to the appended figures, in which:

FIG. 3 is an end elevational view of one exemplary embodiment of a retrievable treat item comprising a center material;

FIG. 4 is an end elevational view of one exemplary embodiment of a hollow retrievable treat item with no center material;

FIG. 5 is an end elevational view of a cross-section of one exemplary embodiment of a solid retrievable treat item with a plurality of shell voids;

FIG. 10b is a top plan view of a retrievable treat item defining a stick having redwood bark surface ornamentation;

FIG. 10c is a bottom plan view of a retrievable treat item defining a stick having redwood bark surface ornamentation;

Figure 1:
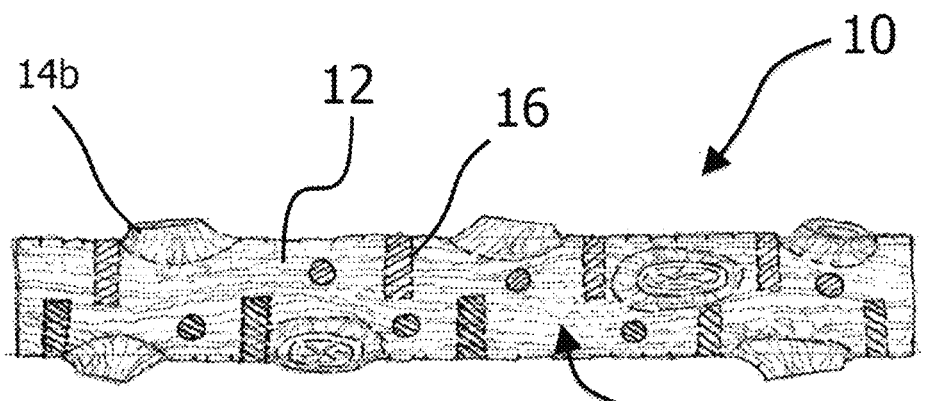
FIG. 1 is a first side elevational view of one exemplary embodiment of a retrievable treat item comprising a plurality of shell voids defining shell pockets.
Figure 2:
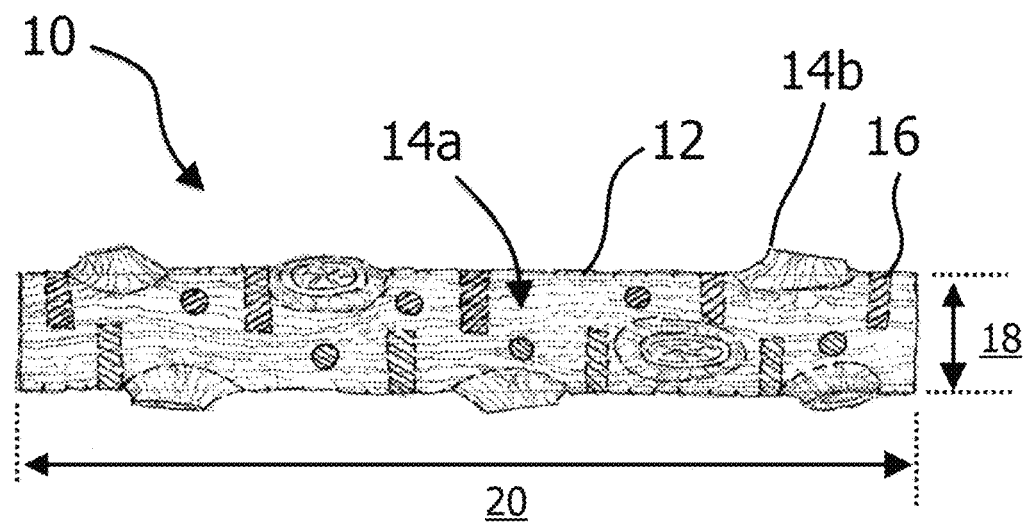
FIG. 2 is a second side elevational view of one exemplary embodiment of a retrievable treat item comprising a plurality of shell voids.
Figure 6:
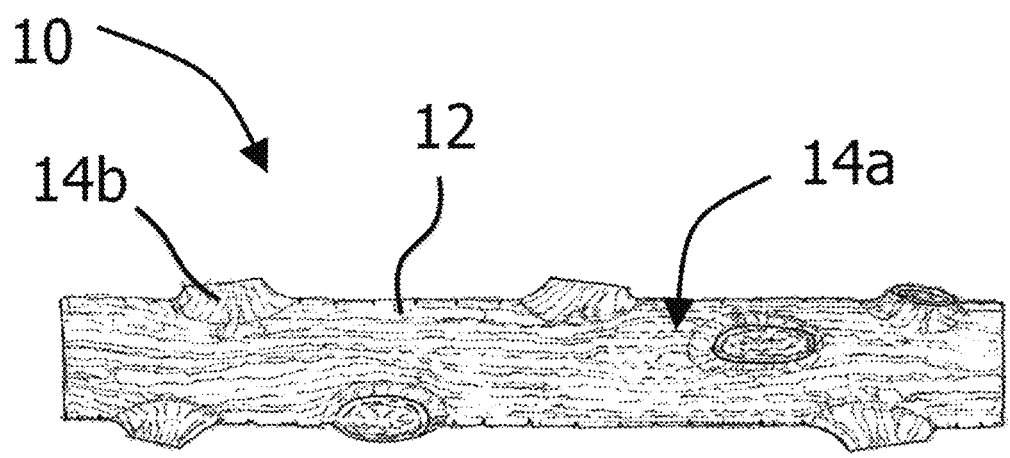
FIG. 6 is a first side elevational view of a retrievable treat item with no shell voids.
Figure 7:
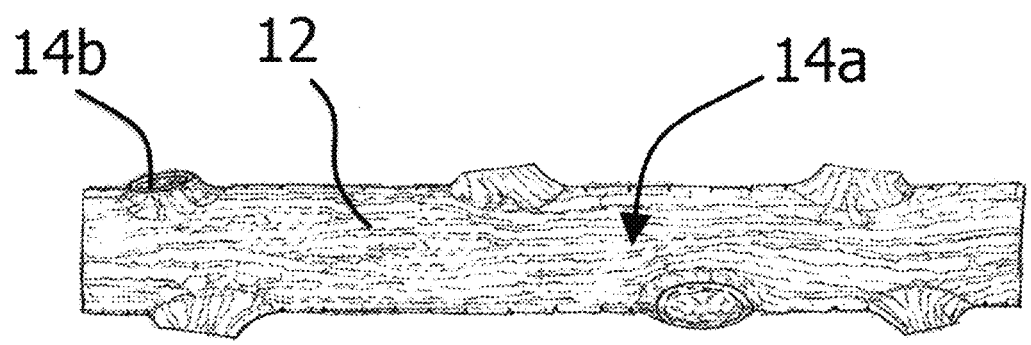
FIG. 7 is a second side elevational view of a retrievable treat item with no shell voids.

Repeat use of reference characters throughout the present specification and appended drawings is intended to represent the same or analogous features or elements of the present technology.

DETAILED DESCRIPTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention covers such modifications and variations as come within the scope of the appended claims and their equivalents. Other objects, features, and aspects of the present invention are disclosed in or may be determined from the following detailed description. Repeat use of reference characters is intended to represent same or analogous features, elements or steps. It is to be understood by one of ordinary skill in the art that the present discussion is a description of exemplary embodiments only and is not intended as limiting the broader aspects of the present invention.

Construction Aids

For the purposes of this document two or more items are "mechanically associated" by bringing them together or into relationship with each other in any number of ways including a direct or indirect physical "releasable connections" (snaps, screws, Velcro®, bolts, etc.—generally connections designed to be easily and frequently released and reconnected), "hard-connections" (welds, rivets, macular bonds, generally connections that one does not anticipate disconnecting very often if at all and that generally needs to be "broken" to separate), and/or "moveable connections" (rotating, pivoting, oscillating, etc.).

For the purposes of this document, unless otherwise stated, the phrase "at least one of A, B, and C" means there is at least one of A, or at least one of B, or at least one of C or any combination thereof (not one of A, and one of B, and one of C).

This document includes headers that are used for place markers only. Such headers are not meant to affect the construction of this document, do not in any way relate to the meaning of this document nor should such headers be used for such purposes.

While the particulars of the present invention and associated technology may be described for use with canines, the disclosed technology may be used for any number of pets and animals including: rabbits, skunks, raccoons, weasels, ferrets, guinea pigs, hamsters, ground hogs, wolverines, potbellied pigs, and/or agriculture animals.

Written Description

Referring now more particularly to FIG. 1 through FIG. 7, one exemplary embodiment of the retrievable treat-item for pets is presented. The retrievable treat-item (10) comprises an outer shell (12) defining at least one hollow section (13, FIG. 4) where the perimeter of the shell (12) defines the general shape of a stick from a plant defining a generally circular outer diameter (18). Notably, for the embodiment in FIG. 4, the hollow section (13) runs the full length of the treat-item (10) although embodiments where the treat-item (10) is only partially hollow fall within the scope and spirit of the invention.

For the current exemplary embodiment, the retrievable treat-item (10) is best used by canines and defines the general shape of a "stick" for larger breeds, "twigs" for medium breeds and "stems" for smaller breads and cats. That said, such sticks, twigs, and stems are formed using the same general process and are collectively referred to as simply "sticks" unless otherwise noted. For the currently preferred embodiment, the overall shell length (20, FIG. 2) is about eight inches with a shell diameter (18) of about one inch (plus or minus 15%). One of ordinary skill in the art will appreciate that the retrievable treat-item (10) may define "bones/sticks" of various shapes and sizes as best suited for the size of the target pet.

The shell (12) comprises a compressed combination of a first-edible-material and a second-edible-material. The shell (12) may define a solid component, a partially hollow component, or a completely hollow shell (FIG. 4). As will be noted later, for one embodiment, shell voids (16, FIG. 1) may also be defined in the shell (12) configured to receive supplements. For the current embodiment, the outer shell (12) comprises ground plant fibers with bone meal additives where the shell is formed by compressing the shell material into the desired form. For the "stick" version such forms will ideally define a textured finish simulating tree bark including at least one of Cypress, Pine, Oak and Redwood. One of ordinary skill in the art will appreciate that other tree shapes and associated bark patterns may be used without departing from the scope and spirit of the invention.

Figure 8:
FIG. 8 is a side elevational view of a retrievable treat item defining a stick having cypress bark surface ornamentation.
Figure 9:
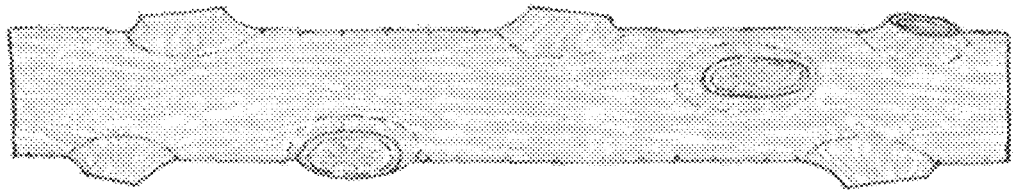
FIG. 9 is a side elevational view of a retrievable treat item defining a stick having oak bark surface ornamentation.
Figure 10:
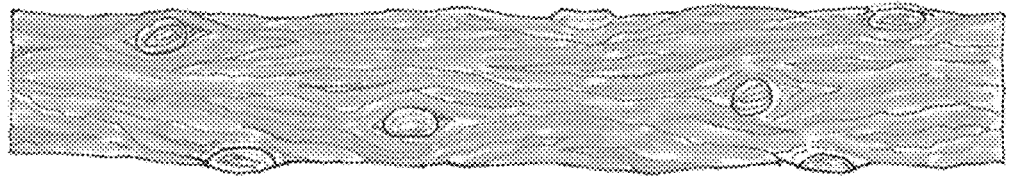
FIG. 10 is a side elevational view of a retrievable treat item defining a stick having redwood bark surface ornamentation.
Figure 11:
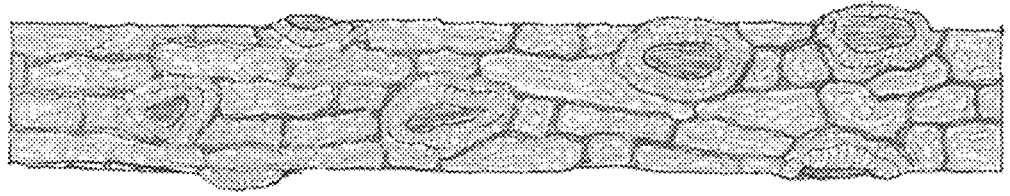
FIG. 11 is a side elevational view of a retrievable treat item defining a stick having pine bark surface ornamentation.
Figure 8B:
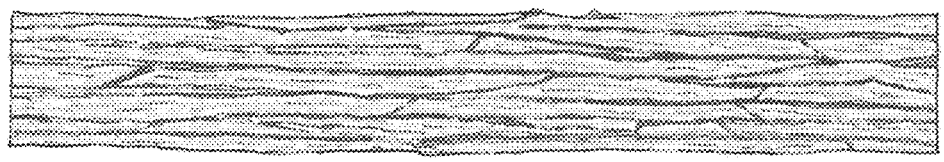
FIG. 8b is a top plan view of a retrievable treat item defining a stick having cypress bark surface ornamentation.
Figure 8C:
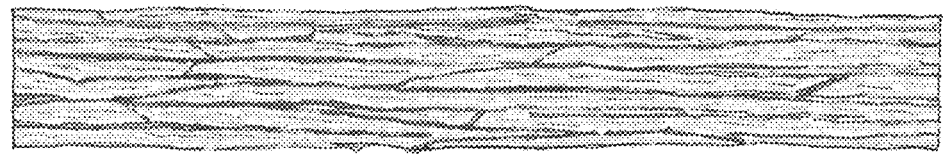
FIG. 8c is a bottom plan view of a retrievable treat item defining a stick having cypress bark surface ornamentation.
Figure 9B:
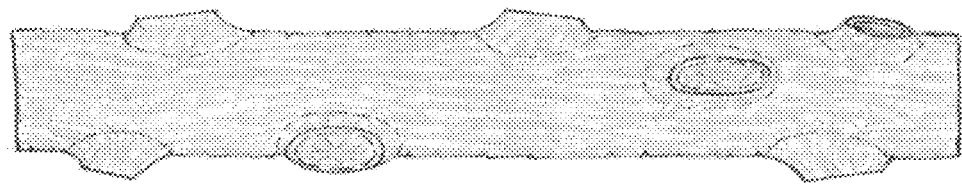
FIG. 9b is a top plan view of a retrievable treat item defining a stick having oak bark surface ornamentation.
Figure 9C:
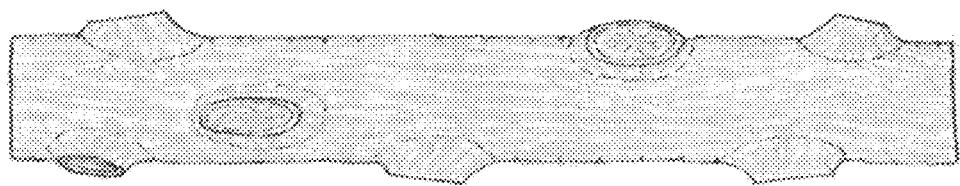
FIG. 9c is a bottom plan view of a retrievable treat item defining a stick having oak bark surface ornamentation.
Figure 10:
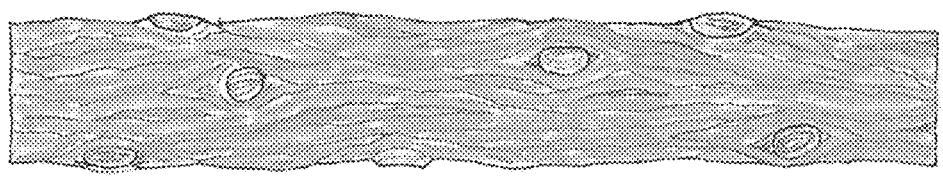
Figure 10:
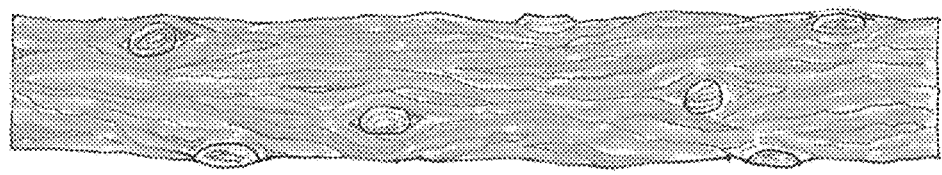
Figure 11B:
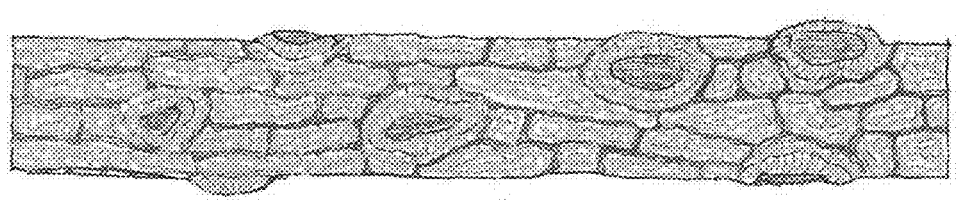
FIG. 11b is a top plan view of a retrievable treat item defining a stick having pine bark surface ornamentation.
Figure 11C:
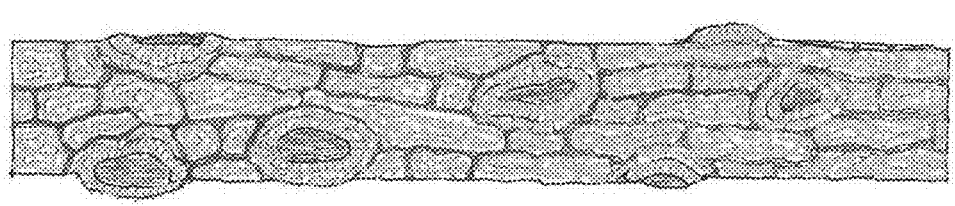
FIG. 11c is a bottom plan view of a retrievable treat item defining a stick having pine bark surface ornamentation.

The component parts of the composite material are pressed to form a shell so that the outer surface of the shell (12) simulates the look of a predefined plant feature (14). One such plant feature is a spur/knot (14b). Another such plant feature (14) is plant bark (14b). The shell material may further be processed to define an associated color. For example, the shell (12) outer surface may resemble (a) a yellowish cypress bark (FIG. 8), (b) a greenish pine bark (FIG. 9), (c) a brownish oak bark (FIG. 10), and/or (d) a reddish redwood bark (FIG. 11). Additionally, one stick design could employ a plurality of bark types along different sections. A shell glaze with a flavored sealant may also be used to give a more realistic appearance. For some embodiments, the bark patterns may define deep ruts and ridges to provide an improved teeth cleaning function.

Typically, where the pet is a dog, a prior art dog "treat" is gobbled down the moment (or within minutes) it is given to the dog. Even longer lasting treats last only minutes, not hours. The average bite strength of dogs is around 270 pounds of pressure. Rottweilers have the strongest average bite strength (330 pounds) while the bite strength of German Shepherds came in second at about (240 pounds). For the preferred embodiment of the present invention, the shell (12) components are selected and processed to provide a shell hardness that results in a minimum consumption period for the target pet. For canines, the preferred predefined consumption period exceeds one day of periodic chewing thereby allowing the retrievable treat-item (10) to be used as a retrievable toy. For such configuration, the shell is configured to withstand the repeated application of an average pressure of 50% of the target pet's average bite strength (in pounds) over a 2.5-inch section of a one-inch diameter shell for about eight hours while being easily digestible once consumed. Such allows for a complete consumption time of about 24 hours of continuous chewing. Such "numbers" are tweaked/modified depending on the size and bite strength of the target pet to achieve similar consumption times and the treat-item may be color coded to give a visual indication of treat durability parameters.

As depicted in FIG. 1 and FIG. 5, for one alternative embodiment, the retrievable treat-item (10) shell (12) defines a solid body, or at least a partially solid body, were a plurality of shield voids (16) are either formed in the solid portion(s) of the shell body or drilled into the shell body to define shell pockets. Such shell pockets are configured to receive supplements and/or the center-material (26) describe below.

Center Material

The retrievable treat-item (10) may further comprise a center-material (26) disposed in a hollow section (13). The center-material (26) preferably defines a nutritious paste that fills the hollow section (13) defined by shell (12). Preferably, the center-material (26) defines a paste filling resembling the meaty center of natural bones and preferably contains a mixture of meat byproducts and plant materials. For one embodiment, calcium and/or bone meal may be added for additional bone health support. Alternatively, fish byproducts or fish oil may be added to provide Omega 3 or 5 fatty acids.

For one embodiment, the center-material (26) is made by mixing cleaned and pulverized hemp leaves and seeds in meat byproducts so that the cleaned and pulverized hemp leaves and seeds are suspended in the meat byproducts to form a paste material.

Embodiments of the above described retrievable treat-item (12) may be designed specifically for dogs and provide for a "HempBone" composed at least partially of hemp to provide the dog with the beneficial support from cannabinoids such as Cannabidiol (CBDs) and cannabinol (CBNs) for treatment of ailments such as arthritis, hip pain, tumor shrinking, leukemia, cancers and organ tissue regeneration; as well as, fiber support for teeth and digestive system health. A viscous version of the product in the form of baby food may be produced for tube feeding pets with more advanced debilitations. Wherever and whenever possible and practical, natural organic processes will be utilized to produce the highest quality results.

Process

One exemplary embodiment for manufacturing a retrievable treat-item (10) is now considered. The first step in the process is to obtain a first-material comprising cleaned and pulverized hemp plants or obtain raw materials and then processing such raw materials accordingly. The second step is to obtain a second-material comprising bone meal. A first mixture is created by combining the first and second material with an organic binder and water to define a first composite material. Such first composite material is compressed in a form and cured to define shell (12). As noted previously, for one embodiment the shell (12) defines an at least a partially hollow structure and may define a solid structure. For the solid structure embodiment, either a plurality of holes (28) are formed by the shell forming process or a plurality of holes (28) are drilled into the shell to define shell pockets. Such shell pockets are configured to receive pet supplements as described above.

For the currently preferred embodiment, the first composite material is composed of about 50 to 60 percent of the first-material and about 20 to 30 percent of the second-material and about 2 to 10 percent of the organic binder. The form is suitably configured so that the other surface of shell (12) defines a first plant feature such as bark or a spur/knot.

For shell (12) embodiments containing at least one hollow section, such hollow section is filled with a second mixture. The next step in the process is to obtain one of (a) compressed and cleaned pulverized hemp leaves and seeds and (b) raw hemp leaves and seeds where such raw hemp leaves and seeds are cleaned and pulverized. Next, meat byproducts are acquired and mixed with the process hemp leaves and seeds so that the cleaned and pulverized hemp leaves and seeds are suspended in said meat byproducts. The hollow shell (12) is filled with the second mixture. The shell pockets may also be filled with the second mixture for some embodiments.

Preferably, the materials used come from fibrous plants such as the corn, sunflower, sorghum, sugarcane, and hemp and their byproducts such as leaves, stems, stalks and seeds. In the case of hemp production of such treat-item, the food preferably contains about 5% to about 40% beneficial cannabinoids for the treatment of various physical conditions ailments, or diseases (chronic and acute).

For one production process, an initial preparation step shall include the cleaning of the raw materials by stream bath (or similar process) to remove contaminants and help start the breakdown of plant material. Cleansing agents may be added to the process such as distilled vinegar, peroxide or baking soda to help aid with the preparation process.

The durable shell fiber matrix composite derived from combination ranges of 40%-80% ground plant material or "flour" containing plant fiber strands, 5%-30% bone meal (calcium supplement), 2%-8% moisture content and 1%-5% organic binder material compressed to form shell (12) utilizing autoclave drying method for curing. The shell (12) may be formed with surface ornamentations such a tree bark such as Cypress, Pine, Oak and Redwood (although other tree shapes and associated bark patterns may also be used). Each tree type may also be processed with an associated color. The shell may be glazed with a flavored sealant to give a more realistic appearance. The glaze may also contain a preservative to help lengthen shelf life and/or add waterproofing.

For pets with more advanced debilitations the mixture ideally defines a higher percentage of cannabinoids and may be processed into a viscous mixture depending on the pet's level of debilitation. Preservatives may be utilized, if needed, to achieve a reasonable shelf life for the product.

Ornamental Features

One of ordinary skill in the art will appreciate that many of the retrievable treat-item's (10) external features are determined more by aesthetics than function. For example, the overall length and diameter may be selected to define a typical stick. While the overall size may be a function of the target pet size, the "look" and surface ornamentations are driven mainly by aesthetics. Indeed, the surface ornamentation of retrievable treat-item (10) may be formed to simulate a plant feature such as tree bark. The bark the surface of the shell simulates (if any) is driven mainly by aesthetics as well as whether the shell defines spurs or knots.

For such embodiments, any number of tree barks could be simulated without departing from the scope and spirit of the invention. Exemplary tree bark features include (a) cypress bark (FIG. 8), (b) pine bark (FIG. 9), (c) Oak bark (FIG. 10), and (d) redwood (FIG. 11). As noted previously, a shell glazed with a flavored sealant may also be used to give a more realistic appearance. All such features a concerned more with aesthetics than function.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A retrievable treat-item for pets, said treat item comprising:
    an outer shell defining at least one hollow section consisting of a compressed combination of a first-edible-material consisting of at least one of pulverized hemp leaves and strands so that said first-edible-material contains at least 10% to 80% cannabinoids and a second-edible-material consisting of 5 to 35 percent calcium supplement bone meal with 2 to 8 percent moisture content and 1 to 5 percent organic binder wherein the amounts are based on the total amount of the outer shell material;
    an edible center-material disposed in said at least one hollow section wherein said center-material comprises a paste that fills the said at least one hollow section; and
    wherein the outer shell hardness results in minimum predefined consumption period exceeding 4 hours for an animal with a bite strength of about 270 pounds thereby allowing the treat-item to be used as a retrievable toy.

2. A retrievable treat-item for pets as in claim 1, wherein said edible center-material comprises hemp.

3. A retrievable treat-item for pets as in claim 2, wherein said edible center-material is composed of between 10 to 80 percent pulverized hemp comprising a cannabinoid material wherein the pulverized hemp is suspended in a meat byproduct.

4. A retrievable treat-item for pets as in claim 2, wherein said outer shell defines the general shape of a stick from a plant configured to simulate the look of at least one plant feature wherein said at least one plant feature is at least one of: (a) cypress bark, (b) pine bark, (c) oak bark, and (d) redwood.

5. A retrievable treat-item for pets as in claim 4, wherein said plant feature is at least one of a spur and a knot.

6. A retrievable treat-item for pets as in claim 5, wherein a pet supplement is disposed in at least one of said spur and said knot.

7. A retrievable treat-item for pets as in claim 2, wherein said shell defines a completely hollow center and wherein said hollow center is filled with said center-material.

8. A retrievable treat-item for pets as in claim 7, wherein said center-material defines a paste filling comprising a mixture of fish byproducts.

9. A retrievable treat-item for pets as in claim 2, wherein the outer shell defines at least one solid portion defining a plurality of voids where at least one void is configured for receiving a pet supplement.

10. A process for making a retrievable treat-stick for pets, said process comprising the steps of:
    obtaining a first-material consisting of at least one of (a) cleaned and pulverized hemp leaves and (b) cleaned and pulverized hemp strands;
    obtaining a second-material consisting of calcium supplement bone meal;
    combining said first-material with said second-material using an organic binder and water to define a first-composite-material consisting of about 50 to 60 percent of said first-material and about 20 to 30 percent of said second-material, about 2 to 8 percent moisture content and about 2 to 10 percent of said organic binder;
    compressing said first-composite-material and curing to define a hard, hollow shell;
    obtaining a hemp-center-product comprising at least one of (a) cleaned and pulverized hemp leaves and strands and (b) cleaned and pulverized hemp seeds;
    obtaining meat byproducts;
    creating a second mixture by mixing said hemp-center-product with said meat byproducts so that the hemp-center-product is suspended in said meat byproducts; and
    filling said hollow shell with said second mixture.

11. A process for making a retrievable treat-stick for pets as in claim 10, wherein the outer shell hardness results in minimum predefined consumption period exceeding four hours thereby allowing the treat-stick to be used as a retrievable toy.

12. A process for making a retrievable treat-stick for pets as in claim 11, wherein said first-composite-material consists of 60 percent of said at least one pulverized hemp leaves and strands and about 30 percent calcium supplement bone meal with about 5 percent moisture content and about 5 percent organic binder.

13. A process for making a retrievable treat-stick for pets as in claim 10, wherein the step of compressing said first-composite-material and curing to define a hard, hollow shell includes making said shell look like a stick wherein the outer surface of said shell defines at least one of: (a) Cypress bark, (b) Pine bark, (c) Oak bark, and (d) Redwood bark.

14. A process for making a retrievable treat-stick for pets as in claim 13, wherein said shell further defines at least one of a spur and a knot.

15. A retrievable treat item for pets, said retrievable treat item comprising:
   an outer shell defining a hollow cylindrical tube wherein said shell consists of a first-edible-material consisting of at least one of pulverized hemp leaves and strands so that said first-edible-material contains at least 10% to 80% cannabinoids and a second-edible-material consisting of calcium supplement bone meal, water and an organic binder;
   a center-material comprising a mixture of meat byproducts having the consistency of a meaty paste wherein said center-material at least partially fills said hollow cylindrical tube; and
   wherein said outer shell is configured to withstand the repeated application of an average pressure of 50% of the target animal's average bite strength for about four hours while being easily digestible once consumed.

16. A retrievable treat item for pets as in claim 15, wherein the outer shell consists of between 40 to 80 percent of said at least one pulverized hemp leaves and strands including the at least 10-80% cannabinoids, 5 to 35 percent calcium supplement bone meal with 2 to 8 percent moisture content and 1 to 5 percent organic binder.

17. A retrievable treat-item for pets as in claim 16, wherein said outer shell defines the general shape of a stick from a plant wherein the outer surface of said shell is configured to simulate the look of at least one of: (a) Cypress bark, (b) Pine bark, (c) Oak bark, and (d) Redwood bark.

18. A retrievable treat item for pets as in claim 17, wherein said shell further define at least one of a spur and a knot.

19. A retrievable treat item for pets as in claim 18, wherein a portion of said hollow cylindrical tube is filled with a center-material comprising mixture of fish byproducts.

* * * * *